United States Patent [19]

Kitamura et al.

[11] Patent Number: 4,816,670
[45] Date of Patent: Mar. 28, 1989

[54] OPTICAL MEASURING HEAD

[75] Inventors: Shiro Kitamura, Ootsu; Junji Koizumi; Kiyoshi Yamada, both of Minami-ashigara, all of Japan

[73] Assignees: Godai Embody Co., Ltd., Osaka; Fuji Photo Film Co., Ltd, Kanagawa, both of Japan

[21] Appl. No.: 98,332

[22] Filed: Sep. 18, 1987

[30] Foreign Application Priority Data

Sep. 19, 1986 [JP] Japan ................................ 61-144991

[51] Int. Cl.$^4$ .............................................. G02B 6/00
[52] U.S. Cl. .................................. 250/227; 350/96.15
[58] Field of Search ............................... 250/216, 227; 350/96.15, 96.29

[56] References Cited

U.S. PATENT DOCUMENTS 4,379,225  4/1983  Apothaker ......................... 250/227

*Primary Examiner*—Edward P. Westin
*Attorney, Agent, or Firm*—Sughrue, Mion, Zinn, Macpeak & Seas

[57] ABSTRACT

An optical measuring head which includes a cylindrical portion having a circular cross section, a plurality of light projecting fibers axially disposed in the cylindrical portion through a predetermined distance, a light receiving fiber provided along an axis of the cylindrical portion, and a convex lens formed, at its outer peripheral portion, with a light receiving face for receiving the light from the light projecting fibers and directing the light through the lens so that the light will be incident upon a flat surface of the lens adjacent an object to be measured, through an angle smaller than a critical angle whereby the light will not be reflected by the flat surface, and disposed at a position coaxial with the light receiving fiber for focusing on a forward end face of the light receiving fiber.

2 Claims, 3 Drawing Sheets

OPTICAL MEASURING HEAD

BACKGROUND OF THE INVENTION

The present invention generally relates to a measuring instrument and more particularly, to an optical measuring head which employs optical fibers.

Conventionally, there has been employed an optical measuring head employing optical fibers for examination, for example, of a blood specimen 8 as shown in FIG. 4 or 7.

The known optical measuring head shown in FIG. 4 includes light projecting fibers 2 axially disposed side by side in a cable, and a light receiving fiber 4 also axially provided within the same cable as illustrated, and is so arranged that reflection of light projected onto the blood specimen 8 which is an object to be measured, from the light projecting fibers 2 is received by the light receiving fiber 4 so as to be transmitted to a measuring device (not shown) for measuring the nature or characteristics of the blood specimen 8 by the amount of the reflected light.

The known optical measuring head as described above, however, has such a problem that it is difficult to effect an accurate examination, since the amount of the reflected light tends to vary upon variation of the distance between said measuring head and the blood specimen 8.

There is also a similar problem in the case where the blood specimen 8 is composed of a transparent protective layer 9, a reacting layer (colored layer) 10, a white reflecting layer 11 and a developing layer 12 disposed one upon another from the side of the measuring head as shown in FIG. 6, and is so arranged that light by the light projecting fibers 2 is led from the transparent protective layer 9 to the reacting layer 10, while the light which has passed through the reacting layer 10 (i.e., the light except for that absorbed by the reacting layer 10) is reflected by the white reflecting layer 11 so as to be incident upon the light receiving fiber 4 through said reacting layer 10 and transparent protective layer 9, whereby the amount of the incident light (indicated by an arrow A in FIG. 6) is to be measured.

More specifically, in the above arrangement of FIG. 6, since light reflected by the transparent protective layer 9 and indicated by an arrow B also enters the light receiving fiber 4, besides the reflected light as indicated by the arrow A referred to above, there is such a disadvantage that an error takes place in the amount of light which has passed through the reacting layer 10 to represent the characteristics of the blood specimen 8, i.e., in the measurement of absorbance of light in the reacting layer 10.

Meanwhile, another conventional optical measuring head shown in FIG. 7 includes the light projecting fibers 2 and light receiving fiber 4 provided in the similar manner as in the measuring head of FIG. 4, and a convex lens 13 disposed in front of the light receiving fiber 4 so as to receive the reflected light from the blood specimen 8 in a converged state, and further, a casing 15 having a transparent glass plate 14 at its forward end and applied over the outer periphery of the head as indicated by two-dotted chain lines depending on necessity.

In the above optical measuring head in FIG. 7 also, there is involved the problem that the result of measurement is affected by the distance between the blood specimen 8 and the measuring head, while the reflected light from the glass 14 besides that by the transparent protective layer 9 enter the light receiving fiber 4 in the similar manner, thus making it difficult to effect an accurate measurement.

SUMMARY OF THE INVENTION

Accordingly, an essential object of the present invention is to provide an improved optical measuring head which is capable of accurately measuring characteristics of an object to be measured, by receiving only reflected light from the object and without being affected by the variation of the distance with respect to said object.

Another object of the present invention is to provide an optical measuring head of the above described type which is simple in construction and stable in functioning, and readily manufactured at low cost.

In accomplishing these and other objects, according to one preferred embodiment of the present invention, there is provided an optical measuring head which includes a cylindrical portion having a circular cross section, a plurality of light projecting fibers axially disposed in the cylindrical portion through a predetermined distance, a light receiving fiber provided along an axis of the cylindrical portion, and a convex lens formed, at its outer peripheral portion, with a light receiving face for receiving the light from the light projecting fibers and directing the light through the lens so that the light will be incident upon the surface of the lens adjacent an object to be measured, at an angle smaller than a critical angle so the light will not be reflected by the surface, and disposed at a position coaxial with the light receiving; fiber for focusing on a forward end face of the light receiving fiber.

By the arrangement according to the present invention as described above, an improved optical measuring head with high reliability has been presented through simple construction.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
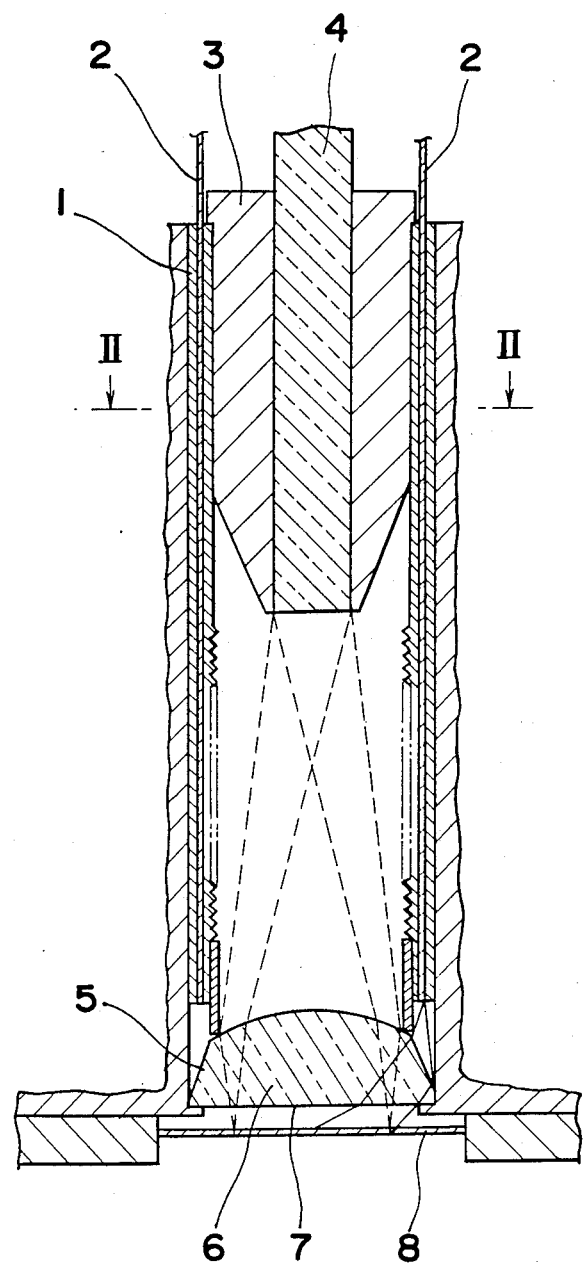
FIG. 1 is a fragmentary longitudinal sectional view of an optical measuring head according to one preferred embodiment of the present invention.

Before the description of the present invention proceeds, it is to be noted that like parts are designated by like reference numerals throughout the accompanying drawings.

Figure 2:
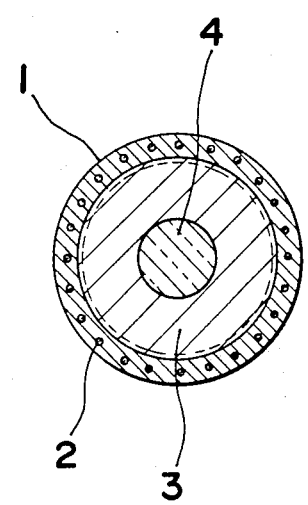
FIG. 2 is a cross section taken along the line II—II in FIG. 1.

Referring now to the drawings, there is shown in FIGS. 1 and 2, an optical measuring head according to one preferred embodiment of the present invention, which generally includes a cylindrical portion 1 having a circular cross section, a plurality of light projecting fibers 2 axially disposed in said cylindrical portion 1 with a predetermined distance therebetween, a light receiving fiber 4 fixed at the axis of said cylindrical portion 1 through a holding member 3, with undulation having a saw-tooth cross section being formed on the inner-surface of the cylindrical portion 1 to prevent light reflection towards the side of the light receiving fiber 4, and a convex lens 6 formed, at its outer peripheral portion, with a light receiving face 5 for receiving the light from the light projecting fibers 2 and directing the light through the lens so as to be incident upon the surface 7 of the lens adjacent an object 8 to be measured, at an angle smaller than a critical angle whereby the light will not be reflected by the surface 7, and disposed at a position coaxial with the light receiving fiber 4 for focusing the light reflected from the object on a forward end face of said light receiving fiber 4.

More specifically, in the above embodiment, the under surface 7 of the convex lens 6 facing the object 8 to be measured is a flat surface, and its upper surface at the opposite side is formed into a curved surface, while the light receiving face 5 thereof is formed into a tapered surface having a straight line in cross section, whereby the light emitted from the light projecting fibers 2 goes through the convex lens 6 without being totally reflected at the under surface 7, and returns to the light receiving fiber 4 after reflection by the object 8 to be measured, for example, the blood specimen 40 located under the measuring head.

Furthermore, as described below, since light which reaches the light receiving fiber 4 is limited to the light incident upon the convex lens 6 at an angle smaller than a predetermined incident angle, there is no possibility that the light reflected by the transparent protective layer 9 of the blood specimen 8 arrives at the light receiving fiber 4, or the amount of light incident upon the light receiving fiber 4 is affected by the distance with respect to the blood specimen 8.

Subsequently, description will further be given with respect to the light incident upon the light receiving fiber 4.

Figure 3:
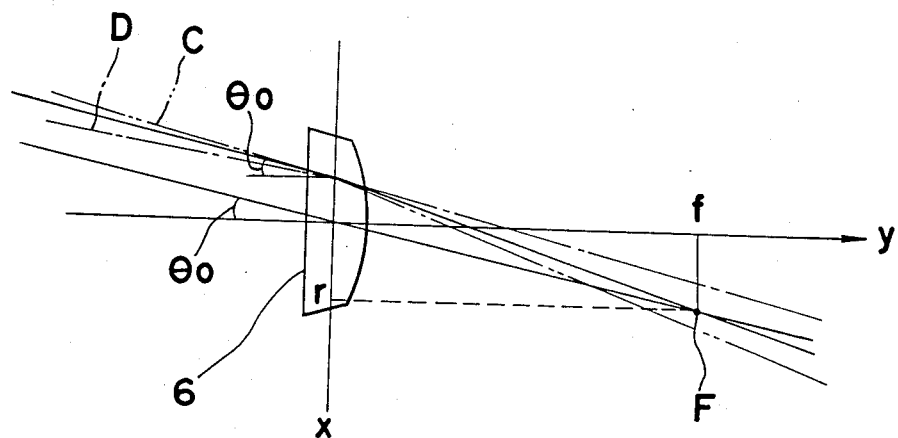
FIG. 3 is a diagram showing relation between an incident angle upon a convex lens and incident light upon a light receiving fiber.
Figure 4:
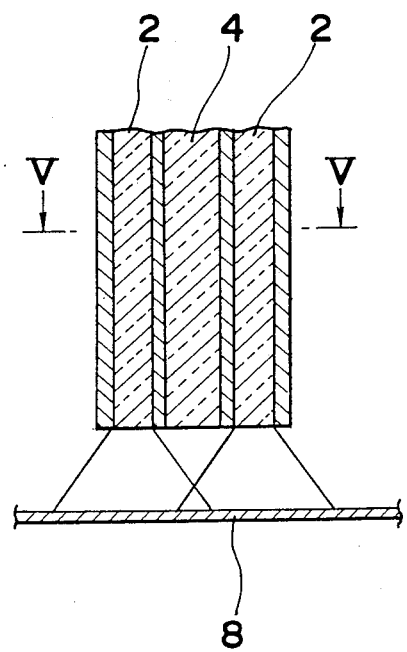
FIG. 4 is a fragmentary longitudinal sectional view of a conventional optical measuring head (already referred to)
Figure 5:
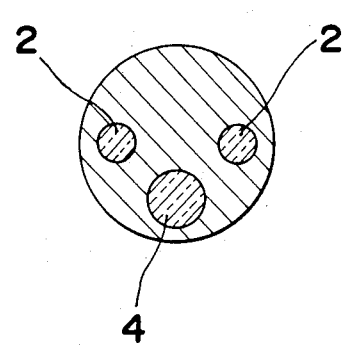
FIG. 5 is a cross section taken along the line V—V in FIG. 4.
Figure 6:
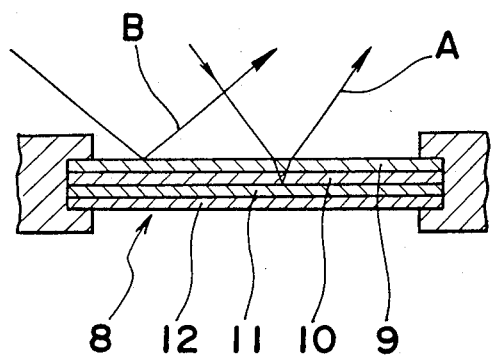
FIG. 6 is a side sectional view showing one example of construction of a blood specimen (already referred to)
Figure 7:
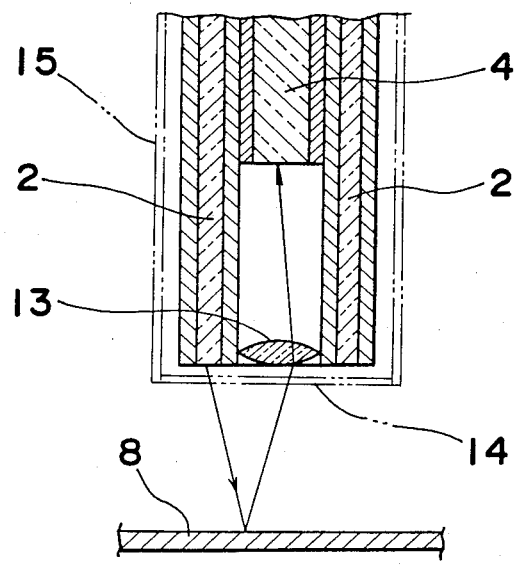
FIG. 7 is a fragmentary longitudinal sectional view of another conventional optical measuring head (already referred to).

As shown in FIG. 3, based on a basic principle of a lens, light incident upon the convex lens 6 at a certain angle, for example, at $\theta_0$ on an arbitrary plane, is focused at a point F spaced by a predetermined distance, for example, by r from an x axis on a straight line $y=f$, where f represents the focal distance. Here, the predetermined distance r is assumed to be a radius of the light receiving fiber 4.

In the diagram of FIG. 3, $\overline{fF}$ corresponds to the forward end face of the light receiving fiber 4, and as in the light represented by a two-dotted chain line C, in the case where the incident angle $\theta$ with respect to the convex lens 6 is in the relation $\theta > \theta_0$, the light transmitted through the convex lens 6 is deviated from the portion $\overline{Ff}$ so as not to be incident upon the light receiving fiber 4, while when the relation is $\theta \leq \theta_0$ as shown by a one-dotted chain line D, the light transmitted through the convex lens 6 passes through the portion $\overline{fF}$ so as to be incident upon the light receiving fiber 4. Thus, owing to the fact that $\tan\theta_0 = r/f$ (constant) and consequently, the angle $\theta_0$ is constant, it is meant that, in the light reflected by one point of the object to be measured, only the light within a predetermined solid angle in which the incident angle upon the convex lens 6 becomes smaller than $\theta_0$, enters the light receiving fiber 4.

Generally, of the reflected light from a certain one point, the amount of light in a predetermined solid angle is reduced in inverse proportion to the square of a distance between said point and the light source, while the area of a plane illuminated by the light source is directly proportional to the square of the above distance, and therefore, the sum of the amount of light within the predetermined solid angle at all points of the irradiated plane becomes constant.

Accordingly, the amount of light entering the light receiving fiber 4 becomes constant irrespective of the distance between the object to be measured and the convex lens 6. Moreover, in the case where the object to be measured is of the blood specimen 8, the light emitted from the light projecting fibers 2 and reflected by the transparent protective layer 9 without reaching the reacting layer 10 and the white reflecting layer 11, protrudes from said predetermined solid angle, without entering said light receiving fiber 4, and thus, the result of the measurement is not affected thereby.

However, for the above relation to be established, it is necessary that all the light from the convex lens 6 is projected onto the object to be measured, while the opening area of the convex lens 6 is so determined that, of the light reflected from the object to be measured, all the light within the predetermined solid angle referred to above is incident upon said convex lens 6 without protrusion.

It should be noted here that, in the foregoing embodiment, although the object to be measured is described as the blood specimen, the present invention is not limited in its application to the measurement of the nature of such blood specimen alone, but may be applied to measurements of characteristics of various other objects.

As is clear from the foregoing description, according to the present invention, the optical measuring head is constituted by the cylindrical portion having a circular cross section, the plurality of light projecting fibers axially disposed in the cylindrical portion through a predetermined distance, the light receiving fiber provided along the axis of the cylindrical portion, and the convex lens formed, at its outer peripheral portion, with the light receiving face for receiving the light from the light projecting fibers and directing the light through the lens so that the light will be incident upon the surface of the lens adjacent the object to be measured, at an angle smaller than the critical angle, and disposed at a position coaxial with the light receiving fiber for focusing on the forward end face of the light receiving fiber.

Owing to the above construction, based on the fundamental principle of the lens as described earlier, even when the distance between the object to be measured and the convex lens, i.e., the optical measuring head, is varied due to, for example, errors in setting the object to be measured, etc., the characteristics of the object to be measured (e.g., besides the state of the blood specimen as described so far, surface conditions such as density, tone of shade, undulation, presence of foreign matter, etc. of various other objects) may be measured without being affected by such variation.

Further, in the case where the object to be measured is, for example, of the blood specimen as described earlier, since it is possible to prevent the reflected light by the transparent protective layer from entering the light receiving fiber, a still more accurate measurement can be effected in cooperation with the earlier-mentioned advantage of not being affected by the distance.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. An optical measuring head which comprises a cylindrical portion having a circular cross section, a plurality of light projecting fibers axially disposed in said cylindrical portion through a predetermined distance, a light receiving fiber provided along an axis of said cylindrical portion, and a convex lens having an outer peripheral portion defining a light receiving face for receiving light from the light projecting fibers and directing the light through the lens so that the light will be incident upon a flat surface of the lens adjacent an object to be measured, at an angle smaller than a critical angle whereby the light will not be reflected by said surface, and disposed at a position coaxial with the light receiving fiber for focusing on a forward end face of said light receiving fiber.

2. An optical measuring head as claimed in claim 1, where said object to be measured is a blood specimen.

* * * * *